(12) United States Patent
Heo (10) Patent No.: US 11,231,907 B2
(45) Date of Patent: Jan. 25, 2022

(54) WEARABLE DEVICE AND METHOD FOR PROVIDING INFORMATION IN A WEARABLE DEVICE

(71) Applicant: LG ELECTRONICS INC., Seoul (KR)

(72) Inventor: Jeong Heo, Seoul (KR)

(73) Assignee: LG ELECTRONICS INC., Seoul (KR)

(*) Notice: Subject to any disclaimer, the term of this patent is extended or adjusted under 35 U.S.C. 154(b) by 133 days.

(21) Appl. No.: 16/726,539

(22) Filed: Dec. 24, 2019

(65) Prior Publication Data
US 2021/0103426 A1    Apr. 8, 2021

(30) Foreign Application Priority Data

Oct. 7, 2019    (KR) .................. 10-2019-0124008

(51) Int. Cl.

| G06F 3/16 | (2006.01) |
|---|---|
| A61B 5/24 | (2021.01) |
| G02B 27/01 | (2006.01) |
| G10L 15/02 | (2006.01) |
| G10L 15/08 | (2006.01) |
| G06F 1/16 | (2006.01) |

(52) U.S. Cl.
CPC .............. *G06F 3/167* (2013.01); *A61B 5/24* (2021.01); *G02B 27/0172* (2013.01); *G06F 1/163* (2013.01); *G06F 1/1694* (2013.01); *G10L 15/02* (2013.01); *G10L 15/08* (2013.01); *G02B 2027/014* (2013.01); *G02B 2027/0138* (2013.01); *G02B 2027/0141* (2013.01); *G02B 2027/0178* (2013.01)

(58) Field of Classification Search
None
See application file for complete search history.

(56) References Cited

U.S. PATENT DOCUMENTS

| 2016/0028917 A1* | 1/2016 | Wexler .............. H04N 5/23206 348/169 |
|---|---|---|
| 2016/0242217 A1* | 8/2016 | Yan ..................... H04L 67/303 |
| 2019/0332168 A1* | 10/2019 | Weldemariam ........ A61B 3/112 |

FOREIGN PATENT DOCUMENTS

WO    WO 2009/086234 A2    7/2009

* cited by examiner

*Primary Examiner* — Stella Higgs
(74) *Attorney, Agent, or Firm* — Birch, Stewart, Kolasch & Birch, LLP (57) ABSTRACT

A method of controlling a wearable device, and which includes obtaining, by a camera of the wearable device, an image including at least a partial field of vision of a user; identifying, by a controller of the wearable device, an object appearing in the image obtained by the camera at a first time point; storing information about the identified object in a memory; detecting, via a microphone of the wearable device, a speech of a user using the wearable device at a second time point; identifying, via the controller, a word included in the detected speech of the user corresponds to the object identified in the image; retrieving, via the controller, the information about the object from the memory based on the identified word included in the detected speech; and outputting the retrieved information about the object.

14 Claims, 7 Drawing Sheets

WEARABLE DEVICE AND METHOD FOR PROVIDING INFORMATION IN A WEARABLE DEVICE

CROSS-REFERENCE TO RELATED APPLICATION

This present application claims benefit of priority to Korean Patent Application No. 10-2019-0124008, entitled "WEARABLE DEVICE AND METHOD FOR PROVIDING INFORMATION IN A WEARABLE DEVICE," filed on Oct. 7, 2019, in the Korean Intellectual Property Office, the entire disclosure of which is incorporated herein by reference.

BACKGROUND OF THE INVENTION

Field of the Invention

The present disclosure relates to a wearable device, and more particularly, to a wearable device for assisting with memory of a user.

Discussion of the Related Art

Wearable devices which use augmented reality are in development. Augmented reality devices provide an augmented reality image in which virtual objects are displayed to be superimposed on a real-world image. Augmented reality devices obtain, from a server, augmented reality data related to an environment in which a user is located, and provide the obtained augmented reality data to the user.

International Patent Publication No. WO 2009/086234 (Related Art 1) discloses an augmented reality system, which provides annotations related to objects or people to a user in real time. The real-time annotation data provided by the augmented reality system disclosed in Related Art 1 may sometimes be irrelevant to data required by a user. However, the continuous providing of information not needed by a user may make the user using an augmented reality device feel fatigued.

SUMMARY OF THE INVENTION

An aspect of the present disclosure is to provide a wearable device capable of automatically collecting information about an object which is present within a field of vision of a user and providing the collected information about the object when the user requires the information.

Another aspect of the present disclosure is to provide a wearable device capable of providing information about an object in response to an explicit query from a user.

Another aspect of the present disclosure is to provide a wearable device capable of providing object information required by a user even when there is no explicit query from the user.

Another aspect of the present disclosure is to provide a wearable device capable of providing information about navigation for arriving at an object when a user requires location information about the object.

The present disclosure is not limited to what has been described above, and other aspects not mentioned herein will be apparent from the following description to one of ordinary skill in the art to which the present disclosure pertains. It is also to be understood that the aspects of the present disclosure may be realized by means and combinations thereof set forth in claims.

Embodiments of the present disclosure identify an object in an image obtained by a camera, store information about the identified object, and provide the information about the object to a user when the user requires the information about the object.

A method of providing information by a wearable device according to an embodiment of the present disclosure includes identifying an object which appears in an image obtained by a camera at a first time point, storing information about the object, identifying a word included in speech of the user at a second time point, and providing the information about the object related to the identified word to the user.

A wearable device according to another embodiment of the present disclosure includes a camera configured to capture an image including at least a partial field of vision of a user, a microphone configured to detect speech of the user, an output device configured to visually or audibly provide information to the user, and a controller. The controller is configured to identify an object which appears in the image captured by the camera at a first time point, store information about the object, detect the speech of the user by using the microphone at a second time point, identify a word included in the speech of the user, and provide the information about the object related to the word to the user by using the output device.

According to an additional embodiment that may be combined with other embodiments of the present disclosure, the detected speech of the user is a speech query requesting the information about the object.

According to an additional embodiment that may be combined with other embodiments of the present disclosure, the information about the object includes at least one of a type the object, a name of the object, a relationship between the object and the user, a location of the object at the first time point, or temporal information about the first time point.

According to an additional embodiment that may be combined with other embodiments of the present disclosure, the information about the user is provided to the user when at least one sensor signal including at least one of an image of a pupil of the user or a biometric signal of the user indicates that the user is flustered at a third time point.

According to an additional embodiment that may be combined with other embodiments of the present disclosure, the object which appears in the image obtained by the camera is identified at the third time point, and the information about the identified object is provided to the user.

According to an additional embodiment that may be combined with other embodiments of the present disclosure, the wearable device includes augmented reality glasses to be mounted on a head of the user.

BRIEF DESCRIPTION OF THE DRAWINGS

The above and other aspects, features, and advantages of the present disclosure will become apparent from the detailed description of the following aspects in conjunction with the accompanying drawings, in which.

DETAILED DESCRIPTION OF THE EMBODIMENTS

The advantages and features of the present disclosure and methods to achieve them will be apparent from the embodiments described below in detail in conjunction with the accompanying drawings. However, the description of particular embodiments is not intended to limit the present disclosure to the particular embodiments disclosed herein, but on the contrary, it should be understood that the present disclosure is to cover all modifications, equivalents and alternatives falling within the spirit and scope of the present disclosure. The embodiments disclosed below are provided so that the present disclosure will be thorough and complete, and also to provide a more complete understanding of the scope of the present disclosure to those of ordinary skill in the art.

The terminology used herein is used for the purpose of describing particular embodiments only and is not intended to be limiting. As used herein, the articles "a," "an," and "the," include plural referents unless the context clearly dictates otherwise. The terms "comprises," "comprising," "includes," "including," "containing," "has," "having" or other variations thereof are inclusive and therefore specify the presence of stated features, integers, steps, operations, elements, and/or components, but do not preclude the presence or addition of one or more other features, integers, steps, operations, elements, components, and/or groups thereof. Furthermore, terms such as "first," "second," and other numerical terms may be used herein only to describe various elements, but these elements should not be limited by these terms. These terms are only used to distinguish one element from another.

An Artificial Neural Network (ANN) is a data processing system modeled after the mechanism of biological neurons and interneuron connections, in which a number of neurons, referred to as nodes or processing elements, are interconnected in layers. ANNs are models used in machine learning and may include statistical learning algorithms conceived from biological neural networks (particularly of the brain in the central nervous system of an animal) in machine learning and cognitive science. ANNs may refer generally to models that have artificial neurons (nodes) forming a network through synaptic interconnections, and acquires problem-solving capability as the strengths of synaptic interconnections are adjusted throughout training. An ANN may include a number of layers, each including a number of neurons. Furthermore, the ANN may include synapses that connect the neurons to one another.

An ANN can be defined by the following three factors: (1) a connection pattern between neurons on different layers; (2) a learning process that updates synaptic weights; and (3) an activation function generating an output value from a weighted sum of inputs received from a previous layer.

An ANN can also include a deep neural network (DNN). Specific examples of the DNN include a convolutional neural network (CNN), a recurrent neural network (RNN), a deep belief network (DBN), and the like, but are not limited thereto. Further, an ANN may be classified as a single-layer neural network or a multi-layer neural network, based on the number of layers therein.

In general, a single-layer neural network includes an input layer and an output layer, and a multi-layer neural network includes an input layer, one or more hidden layers, and an output layer. Further, the input layer receives data from an external source, and the number of neurons in the input layer is identical to the number of input variables. The hidden layer is located between the input layer and the output layer, and receives signals from the input layer, extracts features, and feeds the extracted features to the output layer.

In addition, the output layer receives a signal from the hidden layer and outputs an output value based on the received signal. Input signals between the neurons are summed together after being multiplied by corresponding connection strengths (synaptic weights), and if this sum exceeds a threshold value of a corresponding neuron, the neuron can be activated and output an output value obtained through an activation function. A deep neural network with a plurality of hidden layers between the input layer and the output layer may be the most representative type of artificial neural network which enables deep learning, which is one machine learning technique.

An ANN can be trained using training data. Here, the training refers to the process of determining parameters of the artificial neural network by using the training data, to perform tasks such as classification, regression analysis, and clustering of input data. Such parameters of the artificial neural network may include synaptic weights and biases applied to neurons.

Also, an artificial neural network trained using training data can classify or cluster input data according to a pattern within the input data. Throughout the present specification, an artificial neural network trained using training data is referred to as a trained model.

Hereinbelow, learning paradigms of an artificial neural network will be described in detail. Learning paradigms, in which an artificial neural network operates, can be classified into supervised learning, unsupervised learning, semi-supervised learning, and reinforcement learning. Supervised learning is a machine learning method that derives a single function from the training data. Among the functions that can be derived, a function that outputs a continuous range of values can be referred to as a regressor, and a function that predicts and outputs the class of an input vector can be referred to as a classifier.

In supervised learning, an artificial neural network can be trained with training data that has been given a label. Here, the label refers to a target answer (or a result value) to be guessed by the artificial neural network when the training data is input to the artificial neural network. Also, the target answer (or a result value) to be guessed by the artificial neural network when the training data is input is referred to as a label or labeling data.

In addition, assigning one or more labels to training data in order to train an artificial neural network is referred to as labeling the training data with labeling data. Training data and labels corresponding to the training data together may form a single training set, and as such, they may be input to an artificial neural network as a training set.

Further, the training data can exhibit a number of features, and the training data being labeled with the labels can be interpreted as the features exhibited by the training data being labeled with the labels. In this instance, the training data can represent a feature of an input object as a vector.

Using training data and labeling data together, the artificial neural network can derive a correlation function between the training data and the labeling data. Then, through evaluation of the function derived from the artificial neural network, a parameter of the artificial neural network can be determined (optimized).

Unsupervised learning is a machine learning method that learns from training data that has not been given a label. More specifically, unsupervised learning is a training scheme that trains an artificial neural network to discover a pattern within given training data and performs classification by using the discovered pattern, rather than by using a correlation between given training data and labels corresponding to the given training data.

Examples of unsupervised learning include, but are not limited to, clustering and independent component analysis. Examples of artificial neural networks using unsupervised learning include, but are not limited to, a generative adversarial network (GAN) and an autoencoder (AE).

In more detail, GAN is a machine learning method in which two different artificial intelligences, a generator and a discriminator, improve performance through competing with each other. The generator includes a model generating new data that generates new data based on true data.

In addition, the discriminator is a model recognizing patterns in data that determines whether input data is from the true data or from the new data generated by the generator. Furthermore, the generator can receive and learn from data that has failed to fool the discriminator, while the discriminator can receive and learn from data that has succeeded in fooling the discriminator. Accordingly, the generator can evolve so as to fool the discriminator as effectively as possible, while the discriminator evolves so as to distinguish, as effectively as possible, between the true data and the data generated by the generator.

In addition, an auto-encoder (AE) is a neural network which aims to reconstruct its input as output. More specifically, AE includes an input layer, at least one hidden layer, and an output layer. Since the number of nodes in the hidden layer is smaller than the number of nodes in the input layer, the dimensionality of data is reduced, thus leading to data compression or encoding.

Furthermore, the data output from the hidden layer can be input to the output layer. Given that the number of nodes in the output layer is greater than the number of nodes in the hidden layer, the dimensionality of the data increases, thus leading to data decompression or decoding.

Furthermore, in the AE, the input data is represented as hidden layer data as interneuron connection strengths are adjusted through training. When representing information, the hidden layer can reconstruct the input data as output by using fewer neurons than the input layer can indicate that the hidden layer has discovered a hidden pattern in the input data and is using the discovered hidden pattern to represent the information.

Semi-supervised learning is machine learning method that makes use of both labeled training data and unlabeled training data. One semi-supervised learning technique involves reasoning the label of unlabeled training data, and then using this reasoned label for learning. This technique can be used advantageously when the cost associated with the labeling process is high.

Reinforcement learning is based on a theory that given the condition under which a reinforcement learning agent can determine what action to choose at each time instance, the agent can find an optimal path to a solution solely based on experience without reference to data. Reinforcement learning can be performed mainly through a Markov decision process.

Markov decision process includes four stages: first, an agent is given a condition containing information required for performing a next action; second, how the agent behaves in the condition is defined; third, which actions the agent should choose to get rewards and which actions to choose to get penalties are defined; and fourth, the agent iterates until future reward is maximized, thereby deriving an optimal policy.

An artificial neural network is characterized by features of its model, the features including an activation function, a loss function or cost function, a learning algorithm, an optimization algorithm, and so forth. Also, the hyperparameters are set before learning, and model parameters can be set through learning to specify the architecture of the artificial neural network. For instance, the structure of an artificial neural network can be determined by a number of factors, including the number of hidden layers, the number of hidden nodes included in each hidden layer, input feature vectors, target feature vectors, and so forth.

Hyperparameters include various parameters which need to be initially set for learning, much like the initial values of model parameters. Also, the model parameters include various parameters sought to be determined through learning. For instance, the hyperparameters may include initial values of weights and biases between nodes, mini-batch size, iteration number, learning rate, and so forth. Furthermore, the model parameters may include a weight between nodes, a bias between nodes, and so forth.

Loss function can be used as an index (reference) in determining an optimal model parameter during the learning process of an artificial neural network. Learning in the artificial neural network involves a process of adjusting model parameters so as to reduce the loss function, and the purpose of learning can be to determine the model parameters that minimize the loss function. Loss functions typically use means squared error (MSE) or cross entropy error (CEE), but the present disclosure is not limited thereto.

Cross-entropy error can be used when a true label is one-hot encoded. One-hot encoding includes an encoding method in which among given neurons, only those corresponding to a target answer are given 1 as a true label value, while those neurons that do not correspond to the target answer are given 0 as a true label value.

In machine learning or deep learning, learning optimization algorithms can be deployed to minimize a cost function, and examples of such learning optimization algorithms include gradient descent (GD), stochastic gradient descent (SGD), momentum, Nesterov accelerate gradient (NAG), Adagrad, AdaDelta, RMSProp, Adam, and Nadam.

GD includes a method that adjusts model parameters in a direction that decreases the output of a cost function by using a current slope of the cost function. The direction in which the model parameters are to be adjusted is referred to as a step direction, and a size by which the model parameters are to be adjusted is referred to as a step size. Here, the step size corresponds to a learning rate.

GD obtains a slope of the cost function through use of partial differential equations, using each of model parameters, and updates the model parameters by adjusting the model parameters by a learning rate in the direction of the slope. Further, SGD includes a method that separates the training dataset into mini batches, and by performing gradient descent for each of these mini batches, increases the frequency of gradient descent.

Adagrad, AdaDelta and RMSProp include methods that increase optimization accuracy in SGD by adjusting the step size, and may also include methods that increase optimization accuracy in SGD by adjusting the momentum and step direction. Adam includes a method that combines momentum and RMSProp and increases optimization accuracy in SGD by adjusting the step size and step direction. Nadam includes a method that combines NAG and RMSProp and increases optimization accuracy by adjusting the step size and step direction.

Learning rate and accuracy of an artificial neural network rely not only on the structure and learning optimization algorithms of the artificial neural network but also on the hyperparameters thereof. Therefore, in order to obtain a good learning model, it is preferable to choose a proper structure and learning algorithms for the artificial neural network, but also to choose proper hyperparameters.

In general, the artificial neural network is first trained by experimentally setting hyperparameters to various values, and based on the results of training, the hyperparameters can be set to optimal values that provide a stable learning rate and accuracy. Meanwhile, the artificial neural network can be trained by adjusting connection weights between nodes (if necessary, adjusting bias values as well) so as to produce desired output from given input. Also, the artificial neural network can continuously update the weight values through learning. Furthermore, methods such as back propagation may be used in training the artificial neural network.

Hereinafter, embodiments of the present disclosure will be described in detail with reference to the accompanying drawings. Like reference numerals designate like elements throughout the specification, and overlapping descriptions of the elements will be omitted.

Figure 1:
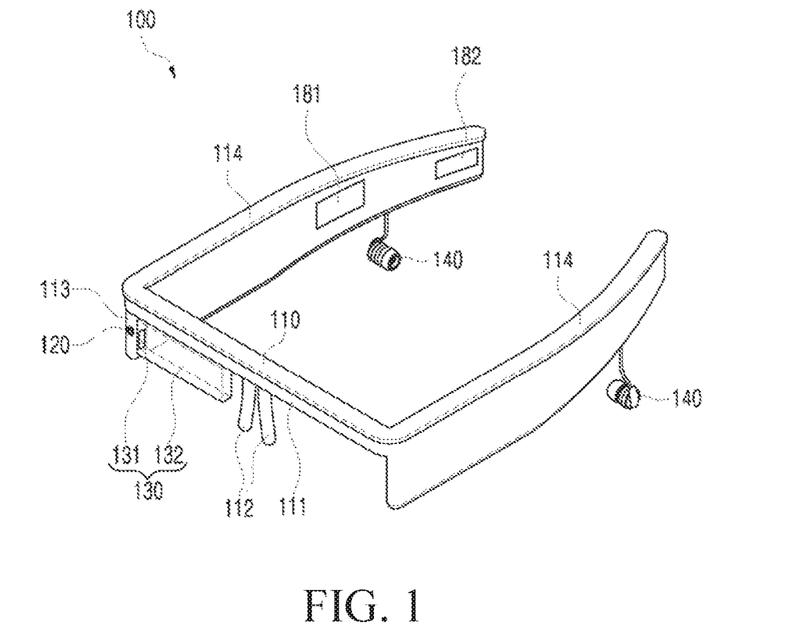
FIG. 1 is a perspective view of a wearable device according to an embodiment of the present disclosure as viewed in a first direction.
Figure 2:
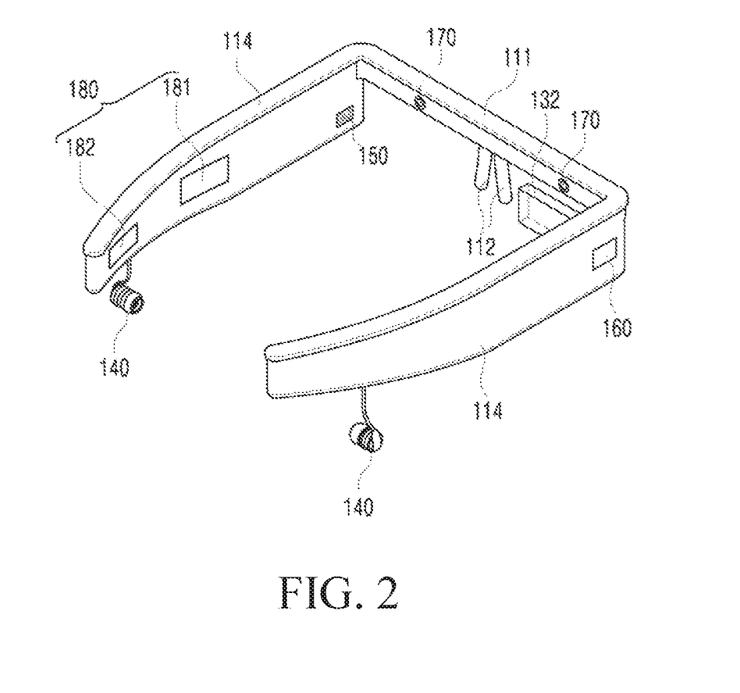
FIG. 2 is a perspective view of a wearable device according to an embodiment of the present disclosure as viewed in a second direction.

FIG. 1 is a perspective view of a wearable device according to an embodiment of the present disclosure as viewed in a first direction, and FIG. 2 is a perspective view of a wearable device according to an embodiment of the present disclosure as viewed in a second direction.

The wearable device according to an embodiment of the present disclosure may be implemented as augmented reality glasses. A wearable device 100 includes a frame 110 formed to be worn on a head of a user. The frame includes a front frame 111 formed to traverse a forehead or eyebrows of the user and a pair of leg frames 114 extending from two ends of the front frame 111 to ears of the user. The front frame 111 includes a nosepad 112 formed to be placed on a nose of the user.

The wearable device 100 includes a front camera 120 configured to capture an image including at least a partial field of vision of the user. The front camera 120 is mounted on the frame 110 so as to be oriented in a direction in which a face of the user faces. The front camera 120, for example, may be mounted on an endpiece 113 connecting the front frame 111 and the leg frame 114.

The wearable device 100 includes an augmented reality (AR) display 130 which is placed within the field of vision of the user when the wearable device 100 is worn by the user. Also, the AR display 130 includes, for example, a transparent display configured to be kept transparent when an electric signal is not applied, and display visual content in a partial region when an electric signal is applied. The term "transparent" used herein not only denotes 100% transmission of light but also denotes partial transmission (for example, at least 10% transmission) of light. That is, the transparent display includes a translucent display.

Further, the AR display 130 includes a projector 131 and a transparent prism 132. As shown, the projector 131 is mounted on the endpiece 113 of the frame 110, and configured to project light towards the prism 132 in response to an electric signal. The prism 132 is disposed within the field of vision of the user, and configured to reflect, towards an eye of the user, at least a portion of light emitted by the projector 131. Also, the prism 132 transmits external light when the projector 131 does not emit light, and the prism 132 combines transmitted external light and the light from the projector 131 when the projector 131 emits the light. Thus, the AR display 130 can display and superimpose visual content generated by the projector 131 on a real-world image.

In addition, the wearable device 100 includes a sound output device 140 configured to convert an electric signal into an acoustic wave to provide a sound to the user. The sound output device 140 includes, for example, an earphone which is insertable into the ears of the user when worn by the user. The sound output device 140 can also be a bone conduction earphone which is not inserted into the ears of the user or a speaker.

The wearable device 100 includes a microphone 150 configured to detect speech of the user to generate an acoustic signal. As shown, the microphone 150 can be disposed on, for example, one of the leg frames 114.

In addition, the wearable device 100 includes a touch input device 160 configured to receive a touch input from the user. The touch input device 160 can be disposed on an outer surface of the right leg frame 114. The touch input device 160 includes at least one of a button or a touch pad.

Further, the wearable device 100 includes a pupil camera 170 configured to detect an image of a pupil to generate a pupil image signal when the wearable device 100 is worn by the user. The pupil camera 170 is mounted in, for example, a rear surface of the front frame 111 at a position corresponding to the eye of the user. Also, the pupil camera 170 can detect a direction and movement of the pupil.

The wearable device 100 includes at least one biometric sensor 180. As show, the biometric sensor 180 may include a pulse sensor 181 configured to come into contact with a temple of the user to detect a pulse and generate a pulse signal. In more detail, the pulse sensor 181 is mounted on the pair of leg frames 114 at a position corresponding to the temple of the user.

The biometric sensor 180 may also include an electroencephalography (EEG) sensor 182 configured to detect a brainwave to generate a brainwave signal. The EEG sensor can be disposed on, for example, a temple tip 115 of the leg frame 114.

Further, the wearable device 100 includes a battery for supplying power to operate the wearable device 100. The battery, for example, can be embedded in the leg frame 114.

The wearable device 100 also includes a wireless transceiver, a location signal receiver, and a controller embedded in the frame 110. The wireless transceiver, the location signal receiver, and the controller are described in detail below with reference to FIG. 3.

Figure 3:
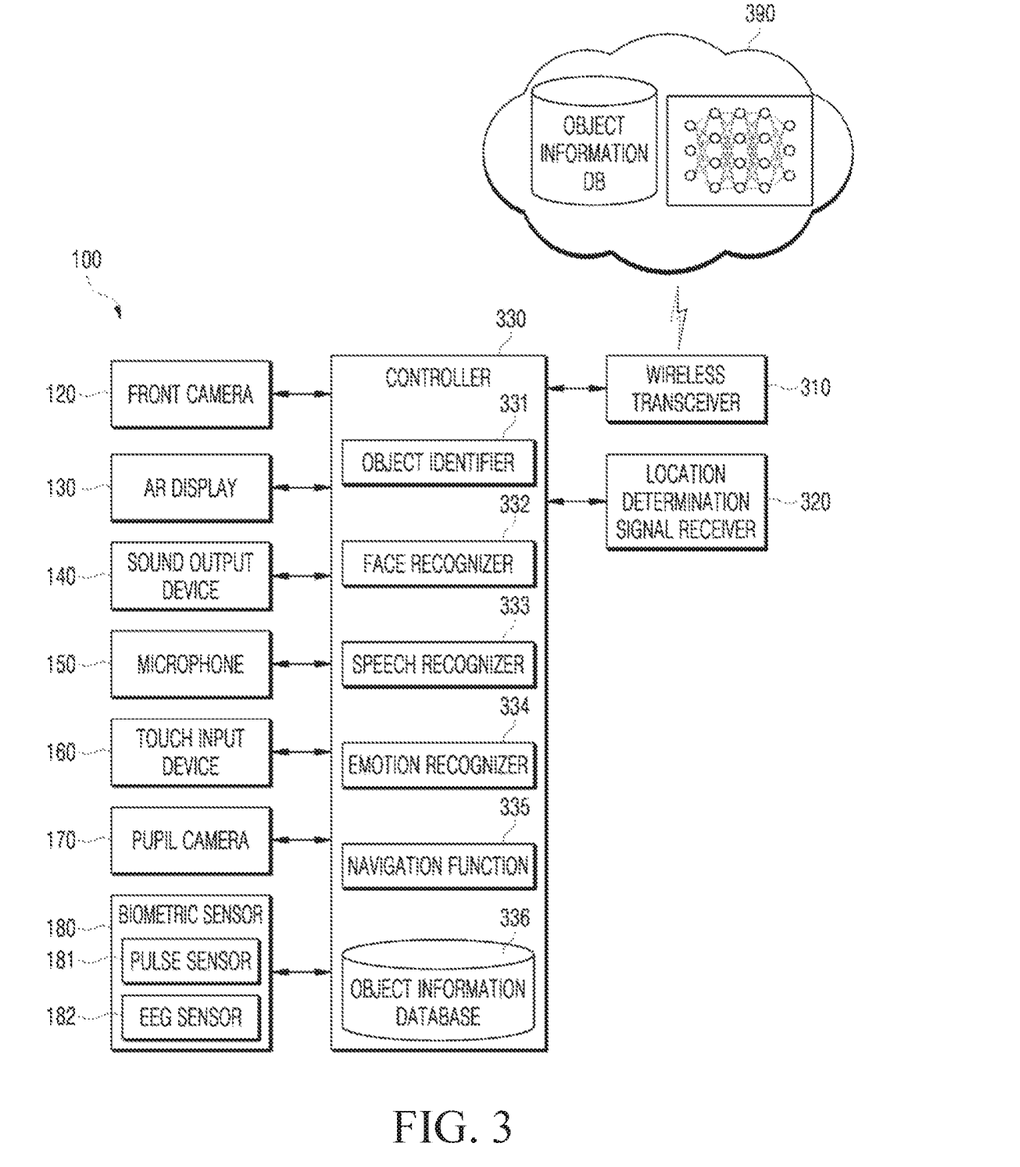
FIG. 3 is a schematic block diagram illustrating a wearable device according to an embodiment of the present disclosure.

Next, FIG. 3 is a schematic block diagram illustrating a wearable device according to an embodiment of the present disclosure. As shown, the wearable device 100 includes a wireless transceiver 310, a location determination signal receiver 320, and a controller 330.

The wireless transceiver 310 is configured to communicate with a remote device, a remote server, an access point, a base station, or a mobile communication core network using at least one wireless communication technology. In particular, the wireless transceiver 310 can communicate with a remote cloud server 390 including an object information database and an artificial neural network configured to analyze at least one of an image, speech, or a biometric signal.

The wireless transceiver 310 may include, but is not limited to, at least one of communication technologies including long-term evolution (LTE), 5th generation (5G) cellular network, Bluetooth, Infrared Data Association (IrDA), Internet of things (IoT), local area network (LAN), low power network (LPN), low power wide area network (LPWAN), personal area network (PAN), radio frequency identification (RFID), ultra-wide band (UWB), wireless fidelity (Wi-Fi), wireless LAN (WLAN), and ZigBee.

The location determination signal receiver 320 is configured to receive a location determination signal to determine a location of the wearable device 100. In addition, the location determination signal receiver 320 includes, for example, a global positioning system (GPS) receiver for receiving a GPS signal from the GPS. The location determination signal receiver 320 can also be integrated in the wireless transceiver 310 to receive a signal from an access point or a base station to determine a location.

In addition, the controller 330 is configured to interact with the front camera 120, the AR display 130, the sound output device 140, the microphone 150, the touch input device 160, the pupil camera 170, the biometric sensor 180, the wireless transceiver 310, and the location determination signal receiver 320 to control operation of the wearable device 100. For example, the controller 330 receives signals from the front camera 120, the microphone 150, the touch input device 160, the pupil camera 170, and the biometric sensor 180, and controls operation of the AR display 130 or the sound output device 140 to provide information visually or audibly to the user. The operation of the wearable device 100 described below may be construed as being performed by the controller 330 unless otherwise explicitly specified.

In addition, the controller 330 may include, for example, at least one processor having a structured circuit to perform functions represented by codes or instructions contained in a program stored in a memory. For example, the at least one processor may include, but is not limited to, at least one of a microprocessor, a central processing unit (CPU), a processor core, a multiprocessor, an image processor, a neural processor, an application-specific integrated circuit (ASIC), or a field programmable gate array (FPGA). The codes or instructions contained in the program stored in the memory may be implemented to perform operation of the controller 330 when executed by the at least one processor.

As shown in FIG. 3, the controller 330 includes an object identifier 331, a face recognizer 332, speech recognizer 333, an emotion recognizer 334, a navigation function 335, and an object information database 336. In more detail, the object identifier 331 is configured to analyze an image signal received from the front camera 120, and identify an object included in the image signal.

Figure 4:
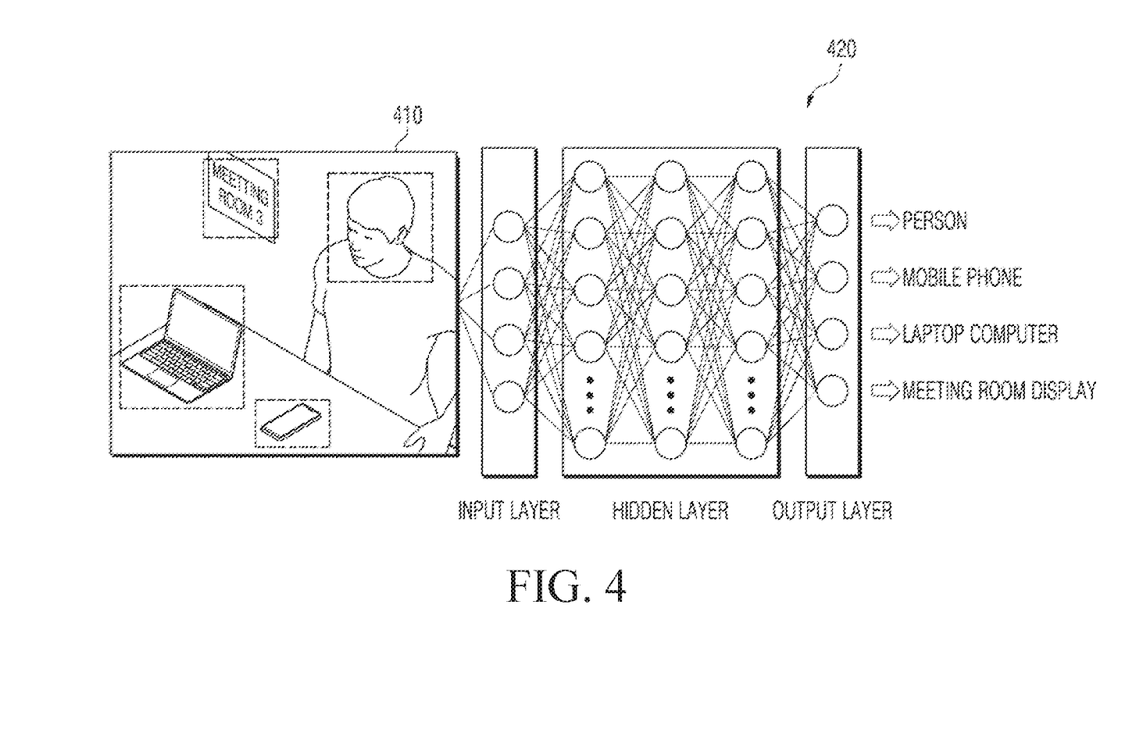
FIG. 4 illustrates an operation of an object identifier according to an embodiment of the present disclosure.

FIG. 4 illustrates an operation of an object identifier according to an embodiment of the present disclosure. The object identifier 331 includes an artificial neural network 420 trained in advance using machine learning so as to identify the type of an object in an image 410 received from the front camera 120. For example, the artificial neural network 420 of the object identifier 331 is trained to identify objects, such as a person, a vehicle, a signboard, and a clock, which are present in the image 410 received from the front camera 120.

The face recognizer 332 is configured to analyze a facial image of a person received from the front camera 120, and identify the person corresponding to the facial image. The face recognizer 332 includes an artificial neural network trained in advance using machine learning so as to identify a person from a facial image. The face recognizer 332 can output an identifier of a recognized person when the recognized person is one who has been previously identified. When the recognized person is a newly identified person, the face recognizer 332 can assign a new identifier to the recognized person.

In addition, the speech recognizer 333 is configured to recognize a meaning of a user's speech received from the microphone 150. The face recognizer 333 includes an artificial neural network trained in advance using machine learning so as to recognize words included in an input speech signal and recognize the meaning of the speech from arrangement of the words. For example, the speech recognizer 333 can recognize speech by using a deep neural network-hidden Markov model (DNN-HMM). The speech recognizer 333 can also output words included in speech, and identify the meaning of the speech as one of predetermined meaning patterns.

Further, the emotion recognizer 334 is configured to estimate an emotional state of the user based on at least one of the user's speech received from the microphone 150, a pupil image received from the pupil camera 170, or a biometric signal (for example, a pulse and a brainwave) received from the biometric sensor 180. The emotion recognizer 334 includes an artificial neural network trained in advance using machine learning so as to determine the emotional state of a person from at least one of speech signal, a pupil image, or a biometric signal. In particular, the emotion recognizer 334 can use multi-modal deep learning for recognizing the emotions of a person from at least two of speech, a pupil image, and a biometric signal.

Figure 5:
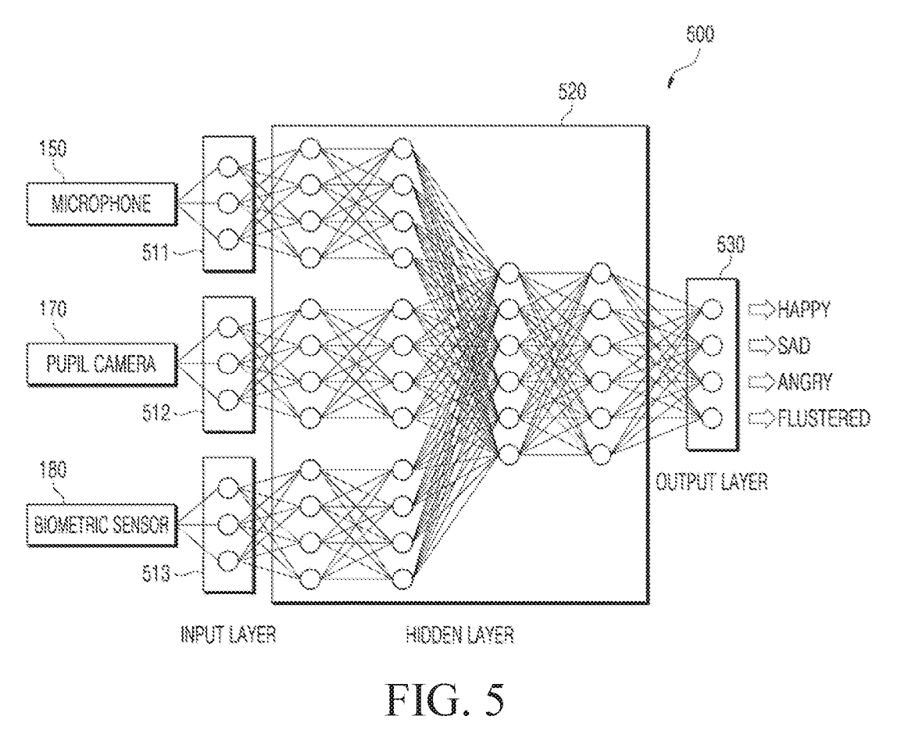
FIG. 5 illustrates a multi-modal deep neural network for an emotion recognizer according to an embodiment of the present disclosure.

FIG. 5 illustrates a multi-modal deep neural network for an emotion recognizer according to an embodiment of the present disclosure. The multi-modal deep learning is a deep learning algorithm for processing a plurality of inputs having different properties, and is intended for improving recognition performance by mutually complementing insufficient information in each signal modality. As shown, a multi-modal deep neural network 500 has separate input layers 511, 512, and 513 for the microphone 150, the pupil camera 170, and the biometric sensor 180. Hidden layers 520 of the multi-modal deep neural network 500 have one or more hidden layers connected to the input layers or hidden layers for different signal modalities. The multi-modal deep neural network 500 has a common output layer 530 for the different signal modalities.

In addition, the navigation function 335 is configured to determine a route to a destination, and provide guidance on the determined route. The navigation function 335 includes at least a map of a surrounding area of the wearable device 100. Also, the navigation function 335 determines a location of the wearable device 100 on the map based on the location determination signal received by the location determination signal receiver 320, and determines a shortest route or optimum route to a destination from the location of the wearable device 100.

Further, the object information database 336 stores information about an object identified by the object identifier 331. The information about an object includes the type of the object, a relationship between the object and the user, a location in which the object has been identified, and a date and time at which the object was identified. When the object is a person, the information about the object may further include an identity (for example, a name or identifier) of the person.

At least one of the object identifier 331, face recognizer 332, speech recognizer 333, emotion recognizer 334, navigation function 335, or object information database 336 can be implemented in the remote cloud server 390. Then, the controller 330 can communicate with the remote cloud server 390 to use the remote cloud server 390 instead of at least one of the object identifier 331, the face recognizer 332, the speech recognizer 333, the emotion recognizer 334, the navigation function 335, or the object information database 336.

Figure 6:
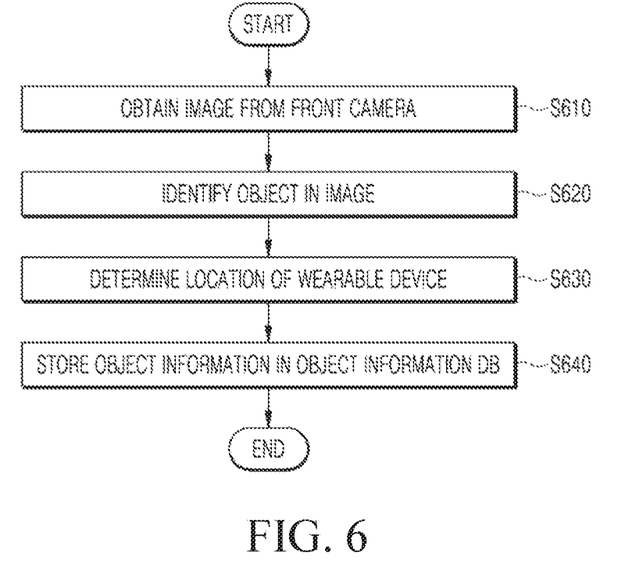
FIG. 6 is a flowchart illustrating a method for collecting object information by a wearable device according to an embodiment of the present disclosure.

Next, FIG. 6 is a flowchart illustrating a method for collecting object information by a wearable device according to an embodiment of the present disclosure. As shown, in operation S610, the wearable device 100 obtains an image from the front camera 120. The image obtained from the front camera 120 includes at least a partial field of vision of the user. Simultaneously, the wearable device 100 obtains a pupil image signal from the pupil camera 171. The wearable device 100 can determine a gazing direction of the user based on the image of the pupil.

In operation S620, the wearable device 100 identifies an object appearing in the image obtained from the front camera 120. The image obtained from the front camera 120 is analyzed by the object identifier 331. In addition, the object identifier 331 inputs the image obtained from the front camera 120 to an artificial neural network trained in advance so as to identify an object included in an image, and identifies the types of objects appearing in the image based on an output from the artificial neural network.

According to an additional embodiment that can be combined with other embodiments of the present disclosure, the wearable device 100 can identify an object which is present in the gazing direction of the user within the image obtained from the front camera 120. In addition, the gazing direction of the user can be determined based on the image of the pupil from the pupil camera 171. For example, the wearable device 100 can identify only an object of a specific area at which the user stares, rather than all of the objects in the image obtained from the front camera 120.

When the image obtained from the front camera 120 is an image of a person, the wearable device 100 identifies the person. A facial image of the person is analyzed by the face recognizer 332. Also, the face recognizer 332 inputs the obtained facial image to an artificial neural network trained in advance so as to identify a person from a facial image, and identifies the person in the image based on an output from the artificial neural network.

In operation S630, the wearable device 100 determines the location of the wearable device 100. The controller 330 determines the location of the wearable device based on the location determination signal received by the location determination signal receiver 320. For example, the controller 330 determines the location of the wearable device 100 based on at least one of a GPS signal from a GPS satellite or a signal from a mobile communication base station in an outdoor environment. The controller 330 also determines the location of the wearable device 100 based on at least one of a beacon signal from a Wi-Fi access point or a signal from a mobile communication base station in an indoor environment.

In operation S640, the wearable device 100 stores information about the identified object in the object information database 336. The information about the object includes the type of the object, the relationship between the object and the user, the location in which the object has been identified, the date and time at which the object was identified, and an image of the object. Further, the wearable device 100 determines the location (for example, latitude and longitude) at which the object has been identified based on the location determination signal from the location determination signal receiver 320, and determines time information (for example, date and time) at which the object was identified based on an internal clock. When the object is a person, the information about the object further includes the identity of the person. The identity of the person includes at least one of the identifier of the person, the name of the person, or the relationship between the identified person and the user.

The wearable device 100 can inquire to the user about additional information which is unidentifiable by the object identifier 331 or the face recognizer 332. In an scenario, the wearable device 100 can make an inquiry by asking, "Is this your wallet?" in order to determine the relationship between the detected object and the user. A speech response of the user can then be recognized by the speech recognizer 333. In another scenario, the wearable device 100 can make an inquiry by asking, "Who is this person?" when a new person is identified, and determine, from a user's response, the name of the identified person or the relationship (for example, family relationship or colleague relationship) between the identified person and the user.

The wearable device 100 also stores, in the object information database 336, the type of the object, the name of the object, the relationship between the object and the user, the location of the object, the time information about the object, and the image of the object obtained by the front camera 120. The object information database can be located in the remote cloud server. In addition, the controller 330 transmits the information about an object to the remote cloud server by using the wireless transceiver 310 in order to store the information about an object in the object information database.

According to an additional embodiment that can be combined with other embodiments of the present disclosure, the controller 330 can store the information about an object in an image when requested by the user. For example, the controller 330 stores, in the object information database, the information about an object which appears in an image when the user touches the touch input device 160.

Figure 7:
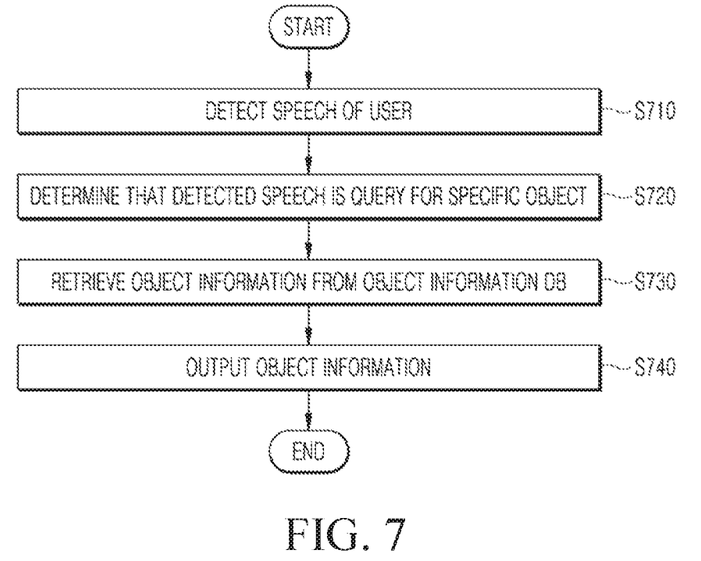
FIG. 7 is a flowchart illustrating a method for providing information by a wearable device according to an embodiment of the present disclosure.

Next, FIG. 7 is a flowchart illustrating a method for providing information by a wearable device according to an embodiment of the present disclosure. In operation S710, the wearable device 100 detects speech of the user based on a sound signal from the microphone 150. For example, the wearable device 100 can determine that the speech of the user is detected when a sound having a magnitude larger than a threshold magnitude is detected in a frequency band of a voice of a human being. In one example, the wearable device 100 can detect the user's speech which says, "Hi LG, where is my laptop computer?"

In operation S720, the wearable device 100 determines that the detected speech of the user is a user query about a specific object. Also, the controller 330 extracts a speech signal of the user by removing components outside the voice frequency band of a human being from a received sound signal. The extracted speech signal of the user is analyzed by the speech recognizer 333, and the speech recognizer 333 determines that the speech of a person is a query about a location of a laptop computer based on an output from a speech recognition model.

In operation S730, the wearable device 100 retrieves, from the object information database, information about an object which is a target for the query. For example, the controller 330 retrieves information about a laptop computer of the user from the local object information database 336 or the remote cloud server 390.

In operation S740, the wearable device 100 outputs retrieved object information, particularly, information about the query, using at least one of the AR display 130 or the sound output device 140. For example, the wearable device 100 can display, on the AR display 130, a location at which the laptop computer of the user was lastly identified by using a dot or arrow on a map together with an image of the laptop computer. The wearable device 100 can also output the object information as speech which says, for example, "The laptop computer is on the table in meeting room 3," by using the sound output device 140.

Figure 8:
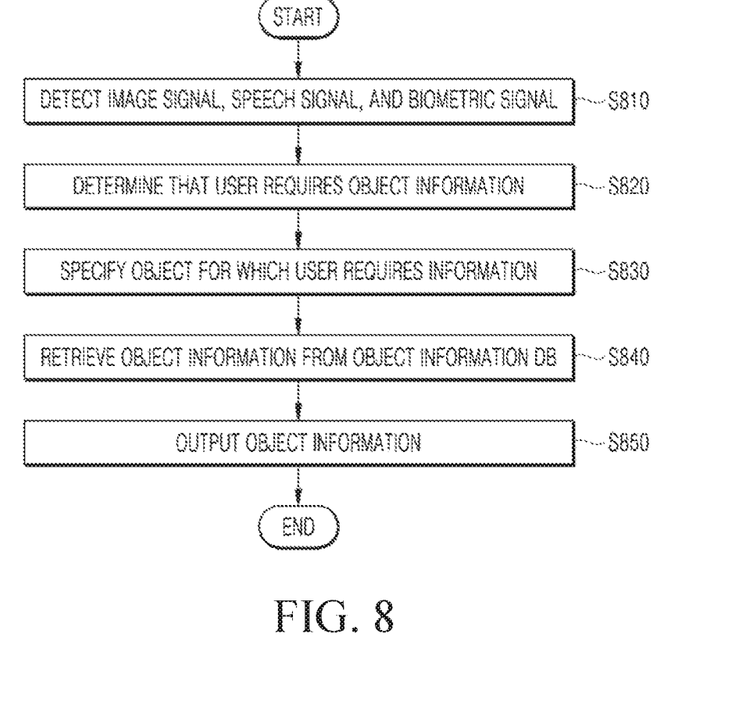
FIG. 8 is a flowchart illustrating a method for providing information by a wearable device according to an additional embodiment of the present disclosure.

Next, FIG. 8 is a flowchart illustrating a method for providing information by a wearable device according to an additional embodiment of the present disclosure. In operation S810, the wearable device 100 monitors a sensor signal from at least one sensor. The at least one sensor includes the front camera 120, the microphone 150, the pupil camera 170, and the biometric sensor 180.

In addition, the wearable device 100 detects speech of the user based on a sound signal from the microphone 150. The wearable device 100 can also determine that the speech of the user is detected when a sound having a magnitude larger than a threshold magnitude is detected in a frequency band of a voice of a human being. In one example, the wearable device 100 can detect the user's speech which says, "Ah! My wallet!" Simultaneously, the wearable device 100 can detect an image of the pupil of the user by using the pupil camera 170, and detect a biometric signal (for example, a pulse or brainwave) of the user by using the biometric sensor 180.

In operation S820, the wearable device 100 determines that the user is flustered based on at least one of a tone in the voice of the user, a movement of the pupil of the user, a change in pulse of the user, or a brainwave change of the user. For example, the wearable device 100 can determine that the user is flustered when the pupil of the user dilates and the pulse of the user increases. The fact that the user is flustered may indicate that the user has lost an object, in other words, the user requires location information about the object.

Whether the user is flustered is analyzed by the emotion recognizer 334. For example, the emotion recognizer 334 can analyze the emotional state of the user by inputting at least one of speech signal from the microphone 150, a pupil image from the pupil camera 170, or a biometric signal from the biometric sensor 180 to, for example, the multi-modal deep neural network.

In operation S830, the wearable device 100 specifies the object for which the user requires information. In more detail, the object for which the user requires information can be specified by the user's speech. In one example, when the wearable device 100 detects the user's speech which says, "Ah! My wallet!" by using the microphone 150, the wearable device 100 can determine that the user has lost a wallet and requires location information about the wallet.

The object for which the user requires information can also be specified by an image from the front camera 120. In another example, the user may be unable to recall a name of a person whom the user has previously met. In this example, the wearable device 100 can determine that the user is staring at a specific person while flustered based on image signals from the front camera 120 and the pupil camera 170, and determine that the user requires information (for example, a name) about the specific person.

In operation S840, the wearable device 100 retrieves information about a specified object from the object information database. In an embodiment, when the user requires the location information about the wallet, the wearable device 100 retrieves the information about the wallet of the user from the object information database by using "user's wallet" as a retrieval query. The wearable device 100 can obtain, from the object information database, the location, date, and time at which the user's wallet was last identified and a last obtained image of the user's wallet.

In another embodiment, when the user requires the name of a person whom the user stares at, the wearable device 100 retrieves information about the person from the object information database by using an image of the person obtained through the front camera 120 as a retrieval query. Here, the wearable device 100 can crop, from the image obtained through the front camera 120, only the image of the person in an area determined to be stared at by the user, and may use a cropped image as a retrieval query. The wearable device 100 can also obtain, from the object information database, the name of the person corresponding to the image, the relationship between the person and the user, and information about the location, date, and time at which the person was last identified.

In operation S850, the wearable device 100 outputs retrieved object information by using at least one of the AR display 130 or the sound output device 140. For example, the wearable device 100 can display, on the AR display 130, the location at which the wallet was lastly identified by using a dot or arrow on a map together with the lastly obtained image of the wallet.

In another example, the wearable device 100 can display, on the AR display 130, information about the person such that the information is superimposed on an actual image of the person. For example, the wearable device 100 can display the name of the person, the relationship between the person and the user, and pieces of additional information in an area of the AR display 130 through which an actual facial image of the person is transmitted.

Figure 9:
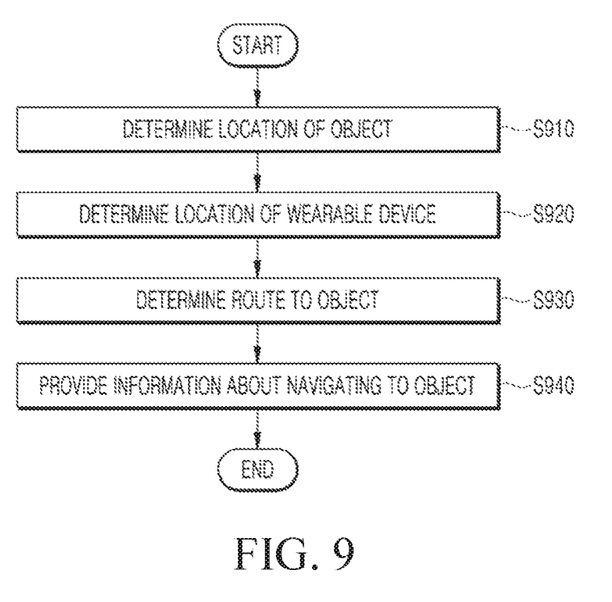
FIG. 9 is a flowchart illustrating a method for providing location information by a wearable device according to an embodiment of the present disclosure.

Next, FIG. 9 is a flowchart illustrating a method for providing location information by a wearable device according to an embodiment of the present disclosure. When the user requires location information about an object, the wearable device 100 provides information about navigating to a location at which the object was lastly identified.

In operation S910, the wearable device 100 determines the location at which the object being searched for by the user was last identified. The location of the object can be obtained from the object information database. In operation S920, the wearable device 100 determines a current location of the wearable device 100. In more detail, the location of the wearable device 100 can be determined based on the location determination signal received by the location determination signal receiver 320.

In operation S930, the wearable device 100 determines a route to the location of the object from the location of the wearable device 100. Further, the navigation function 335 of the wearable device 100 can determine a shortest route or optimum route to the location of the object by using map information. In operation S940, the wearable device 100 outputs the information about navigating to the location of the object by using at least one of the AR display 130 and the sound output device 140. The wearable device 100 can display, on the AR display 130, a direction in which the user should travel and a distance that the user should travel by using, for example, an arrow so as to assist the user to efficiently arrive at the location of the object.

Wearable devices according to embodiments of the present disclosure can automatically collect information about an object which is present within a field of vision of a user, and provide the collected information about the object when the user requires the information. Wearable devices according to embodiments of the present disclosure can also provide information about an object required by a user not only when there is an explicit query of the user but also when there is no explicit query of the user.

Further, wearable devices according to embodiments of the present disclosure improve user convenience of by providing, in a navigating manner, location information required by the user.

The example embodiments described above may be implemented through computer programs executable through various components on a computer, and such computer programs may be recorded on computer-readable media. Examples of the computer-readable media include, but are not limited to: magnetic media such as hard disks, floppy disks, and magnetic tape; optical media such as CD-ROM disks and DVD-ROM disks; magneto-optical media such as floptical disks; and hardware devices that are specially configured to store and execute program codes, such as ROM, RAM, and flash memory devices.

Meanwhile, the computer programs may be those specially designed and constructed for the purposes of the present disclosure or they may be of the kind well known and available to those skilled in the computer software arts. Examples of program code include both machine codes, such as produced by a compiler, and higher level code that may be executed by the computer using an interpreter.

As used in the present disclosure (especially in the appended claims), the singular forms "a," "an," and "the" include both singular and plural references, unless the context clearly states otherwise. Also, it should be understood that any numerical range recited herein is intended to include all sub-ranges subsumed therein (unless expressly indicated otherwise) and accordingly, the disclosed numeral ranges include every individual value between the minimum and maximum values of the numeral ranges.

The order of individual steps in process claims according to the present disclosure does not imply that the steps must be performed in this order; rather, the steps may be performed in any suitable order, unless expressly indicated otherwise. The present disclosure is not necessarily limited to the order of operations given in the description. All examples described herein or the terms indicative thereof ("for example," etc.) used herein are merely to describe the present disclosure in greater detail. Therefore, it should be understood that the scope of the present disclosure is not limited to the embodiments described above or by the use of such terms unless limited by the appended claims. Also, it should be apparent to those skilled in the art that various modifications, combinations, and alternations can be made depending on design conditions and factors within the scope of the appended claims or equivalents thereof.

The present disclosure is not limited to the example embodiments described above, and rather intended to include the following appended claims, and all modifications, equivalents, and alternatives falling within the spirit and scope of the following claims.

What is claimed is:

1. A method of controlling a wearable device, the method comprising:
    obtaining, by a camera of the wearable device, an image including at least a partial field of vision of a user;
    identifying, by a controller of the wearable device, an object appearing in the image obtained by the camera at a first time point;
    storing information about the identified object in a memory;
    detecting, via a microphone of the wearable device, a speech of the user using the wearable device at a second time point;
    identifying, via the controller, a word included in the detected speech of the user corresponds to the object identified in the image;
    obtaining, by a pupil camera of the wearable device, an image of a pupil of the user at a third time point;
    determining, via the controller, that the user is flustered by using an artificial neural network trained in advance so as to recognize an emotional state of the user from the image of the pupil of the user;
    retrieving, via the controller, the information about the object from the memory based on the identified word included in the detected speech;
    outputting the retrieved information about the object to the user in response to the determining that the user is flustered,
    wherein the outputting the retrieved information about the object comprises:
    when the object corresponds to a personal item of the user and the identified word corresponds to the personal aero of the user, determining, by a location processor of the wearable device, a location of the wearable device and outputting information about navigating from the determined location to a location at which the object was identified at the first time point; and
    when the object corresponds to a person and the identified word corresponds to the person, outputting information about the object comprising a name of the person, and a relation strip between the person and the user.

2. The method of claim 1, wherein the speech of the user is a speech query requesting the information about the object.

3. The method of claim 1, wherein the information about the object comprises at least one of a type of the object, a name of the object, a relationship between the object and the user, a location of the object at the first time point, or temporal information about the first time point.

4. The method of claim 1, wherein the outputting the information about the object comprises:
    identifying the object appearing in the image obtained by the camera at the third time point; and
    outputting the information about the object identified at the third time point to the user.

5. The method of claim 1, further comprising:
    obtaining, by a biometric sensor, a biometric signal of the user, at a third time point;
    determining, via the controller, that the user is flustered by using an artificial neural network trained in advance so as to recognize an emotional state of the user from the biometric signal; and outputting the information about the object to the user in response to the determining that the user is flustered.

6. The method of claim 5, wherein the outputting the information about the object comprises:
identifying the object appearing in the image obtained by the camera at the third time point; and
outputting the information about the object identified at the third time point to the user.

7. A wearable device comprising:
a camera configured to capture an image including at least a partial field of vision of a user;
a microphone configured to detect speech of the user wearing the wearable device;
an output device configured to visually or audibly provide information to the user;
a pupil camera configured to capture an image of a pupil of the user; and
a controller configured to:
identify an object appearing in the image captured by the camera at a first time point;
store information about the object in a memory;
detect the speech of the user using the wearable device by using the microphone at a second time point;
identify a word included in the detected speech of the user corresponds to the object identified in the image;
determine that the user is flustered at a third time point by using an artificial neural network trained in advance so as to recognize an emotional state of the user from the image of the pupil of the user;
retrieve the information about the object from the memory based on the identified word included in the detected speech; and
output the retrieved information about the object to the user in response to the determination that the user is flustered,
wherein the controller is further configured to:
when the object corresponds to a personal item of the user and the identified word corresponds to the personal item of the user, determine, by a location processor of the wearable device, a location of the wearable device and output information about navigating from the determined location to a location at which the object was identified at the first time point; and
when the object corresponds to a person and the identified word corresponds to the person, output information about the object comprising a name of the person, and a relationship between the person and the user.

8. The wearable device of claim 7, wherein the speech of the user is a speech query requesting the information about the object.

9. The wearable device of claim 7, wherein the information about the object comprises at least one of a type of the object, a name of the object, a relationship between the object and the user, a location of the object at the first time point, or temporal information about the first time point.

10. The wearable device of claim 7, wherein the controller is further configured to:
identify the object appearing in the image obtained by the camera at the third time point; and
output the information about the object identified at the third time point to the user.

11. The wearable device of claim 7, further comprising:
a biometric sensor configured to obtain a biometric signal of the user at a third time point,
wherein the controller is further configured to:
determine the user is flustered by using an artificial neural network trained in advance so as to recognize an emotional state of the user from the biometric signal; and
output the information about the object to the user in response to the determining that the user is flustered by using the output device.

12. The wearable device of claim 11, wherein the controller is further configured to:
identify the object appearing in the image obtained by the camera at the third time point; and
output the information about the object identified at the third time point to the user by using the output device.

13. The wearable device of claim 7, wherein the output device comprises at least one of:
an augmented reality display disposed within the field of vision of the user when the wearable device is worn by the user, and configured to display visual content superimposed on a real-world image; or
a sound output device configured to provide an auditory stimulation to the user when the wearable device is worn by the user.

14. The wearable device of claim 7, wherein the wearable device comprises augmented reality glasses to be mounted on a head of the user.

* * * * *